US012742774B2

(12) United States Patent
Tyler et al.

(10) Patent No.: US 12,742,774 B2
(45) **Date of Patent: *Sep. 22, 2026**

(54) METHODS FOR DETECTING ABERRANT RESULTS CAUSED BY INCOMPLETE DELIVERY OF A POLYHAPTEN REAGENT IN IMMUNOASSAYS

(71) Applicant: Siemens Healthcare Diagnostics Inc., Tarrytown, NY (US)

(72) Inventors: Amy Tyler, Lincoln University, PA (US); Tie Wei, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 937 days.

This patent is subject to a terminal disclaimer.

(21) Appl. No.: 17/594,470

(22) PCT Filed: Feb. 3, 2020

(86) PCT No.: PCT/US2020/016371

§ 371 (c)(1),
(2) Date: Oct. 18, 2021

(87) PCT Pub. No.: WO2020/236233

PCT Pub. Date: Nov. 26, 2020

(65) Prior Publication Data

US 2022/0196640 A1 Jun. 23, 2022

Related U.S. Application Data

(60) Provisional application No. 62/850,218, filed on May 20, 2019.

(51) Int. Cl.

| | |
|---|---|
| ***G01N 33/72*** | (2006.01) |
| ***G01N 21/27*** | (2006.01) |
| ***G01N 21/82*** | (2006.01) |
| ***G01N 33/53*** | (2006.01) |

(52) U.S. Cl.

CPC ......... *G01N 33/5306* (2013.01); *G01N 21/82* (2013.01); *G01N 33/723* (2013.01)

(58) Field of Classification Search

CPC ............... G01N 33/5306; G01N 21/82; G01N 33/723; G01N 21/272

See application file for complete search history.

(56) References Cited

U.S. PATENT DOCUMENTS

| | | | | |
|---|---|---|---|---|
| 6,043,043 | A | 3/2000 | Yip | |
| 2009/0291464 | A1 | 11/2009 | Iwata | |
| 2011/0070658 | A1 | 3/2011 | Rutter et al. | |
| 2015/0044780 | A1 | 2/2015 | Kurz et al. | |
| 2021/0270849 | A1* | 9/2021 | Wei | G01N 33/723 |

FOREIGN PATENT DOCUMENTS

| | | |
|---|---|---|
| CN | 102427828 | 4/2012 |
| CN | 108593641 | 9/2018 |
| JP | H06308122 | 4/1994 |
| JP | 0666795 | 9/1994 |
| JP | 0735752 | 2/1995 |
| JP | 2003329551 | 11/2003 |
| JP | 2009042057 | 2/2009 |
| JP | 2015515005 | 5/2015 |
| JP | H6-308122 | 4/2018 |
| JP | 7401559 | 12/2023 |
| WO | 03050292 | 6/2003 |
| WO | 2016196638 | 12/2016 |

OTHER PUBLICATIONS

Hamwi et al. "Quantitative Measurement of HbA1c by an Immunoturbidimetric Assay Compared to a Standard HPLC Method", Clinical Chemistry, vol. 104, No. 1, pp. 89-95, published Jul. 1995. (Year: 1995).*

Genc et al. "Evaluation of Turbidimetric Inhibition Immunoassay (TINIA) and HPLC Methods for Glycated Haemoglobin Determination", Journal of Clinical Laboratory Analysis, vol. 26, pp. 481-485, published 2012. (Year: 2012).*

Chang et al. "Evaluation and Interference Study of Hemoglobin A1c Measured by Turbidimetric Inhibition Immunoassay", Hematopathology, vol. 109, No. 3, pp. 274-278, published Mar. 1998 (Year: 1998).*

Wauthier et al. "Interferences in immunoassays: review and practical algorithm", Clin Chem Lab Med 2022; vol. 60(6): pp. 808-820 , published Mar. 18, 2022 (Year: 2022).*

Dimeski et al. "Paraprotein interference with turbidimetric gentamicin assay", Biochemia Medica, 2015; vol. 25(1): pp. 117-124 (Year: 2015).*

Voutsinas et al. "A simple Turbidimetric Method for Determining the Fat Binding Capacity of Proteins", J. Agric. Food Chem., vol. 31, No. 1, pp. 58-63, published 1983 (Year: 1983).*

Thaler, Leonard M., et al. "Diabetes in urban African-Americans. XVII. Availability of rapid HbA1c measurements enhances clinical decision-making." Diabetes care, 22.9 (1999): 1415-1421.

Miller, Christopher D., et al. "Rapid A1c availability improves clinical decision-making in an urban primary care clinic." Diabetes care, 26.4 (2003): 1158-1163.

Karl J. et al: "Development and Standardization of a New Immunoturbidimetric HbA1c Assay"; Klinisches Labor; vol. 39, No. 12, Jan. 1, 1993 (Jan. 1, 1993), pp. 991-996.

Anonymous: "Tina-quant HbA1c Gen. 3"; Internet Article; Jan. 1, 2013 (Jan. 1, 2013), pp. 1-2.

Chang, Judy et al: "Evaluation and Interference Study of Hemoglobin A1c Measured by Turbidimetric Inhibition Immunoassay"; Hematopathology; vol. 109, No. 3, Mar. 1, 1998, pp. 274-278.

Wang Yao et al:"Analysis of different pre-treatments of samples on results of glycated hemoglobin detection", p. 2216+2218, Oct. 28, 2010, English Machine Translation provided.

International Search Report for PCT/US2020/016371 dated Feb. 3, 2020.

Bangs Laboratories Publication; "Ask The Particle Doctor"; last update Mar. 11, 2011; vol. 12; No. 1; 1-27; Retrieved on Sep. 10, 2019 from the internet; p. 30., par. 6 and 7; vol. 14, #2, Jun. 2001.

(Continued)

*Primary Examiner* — Shafiqul Haq
*Assistant Examiner* — Nam P Nguyen

(57) ABSTRACT

Methods of detecting aberrant results caused by delivery issues for a polyhapten reagent in the context of immunoassays are disclosed.

15 Claims, 4 Drawing Sheets

(56) References Cited

OTHER PUBLICATIONS

Siemens Healthcare Diagnostics K.K.; package insert for Glycohemoglobin A1c Kit Flex Cartridge Hemoglobin A1c VIFCC, Dec. 2017.

* cited by examiner

METHODS FOR DETECTING ABERRANT RESULTS CAUSED BY INCOMPLETE DELIVERY OF A POLYHAPTEN REAGENT IN IMMUNOASSAYS

CROSS REFERENCE TO RELATED APPLICATIONS/INCORPORATION BY REFERENCE STATEMENT

Not Applicable.

STATEMENT REGARDING FEDERALLY SPONSORED RESEARCH OR DEVELOPMENT

Not Applicable.

BACKGROUND

Accurate control of blood glucose can ameliorate much of the morbidity and mortality associated with diabetes mellitus. Therefore, many different assays for hemoglobin have been developed, based on the physical and chemical properties of hemoglobin or based on specific antibody-recognized epitopes thereof. Clinical studies have shown that HbA1c results improve decision making, patient compliance, and outcomes (Thaler et al. (Diabetes Care (1999) 22:1415-1421); and Miller et al. (Diabetes Care (2003) 26:1158-1163)).

Immunoassays are currently the most common type of hemoglobin assays used in the clinical laboratory setting. These immunoassay methods utilize antibodies that recognize an epitope of hemoglobin, and in particular instances, an epitope of glycated hemoglobin (HbA1c), such as (but not limited to) at least a portion of the N-terminal glycated amino acids thereof. For example, the turbidimetric inhibition immunoassay (TINIA) for the analyte HbA1c utilizes an R1 reagent (i.e., an anti-HbA1c antibody) and an R2 polyhapten reagent (i.e., a synthetic molecule that contains multiple HbA1c epitopes to cause agglutination with free antibody). When no HbA1c analyte is present, the polyhapten reacts with free anti-HbA1c antibodies to form an insoluble antibody-polyhapten complex, and this results in turbidity and light scattering when the sample is illuminated with the light source. When the target analyte HbA1c is present in a biological sample (such as, but not limited to, a whole blood sample), the HbA1c analyte reacts with the anti-HbA1c antibody and forms a soluble analyte-antibody complex that reduces the amount of light scatter observed. The rate of the reaction can be measured turbidimetrically and is inversely proportional to the amount of HbA1c analyte present in the biological sample.

A major concern for this immunoassay involves delivery issues with the R2 polyhapten reagent, such as (but not limited to) short delivery or a broken air bubble, that cause aberrant results to be reported. R2 is a polypeptide solution that absorbs at 293 nm, a wavelength that is available on multiple clinical chemistry analyzers, such as (but not limited to) the DIMENSION VISTA® Systems (Siemens Healthcare Diagnostics Inc., Tarrytown, NY); however, there are no available read times immediately after the addition of the polyhapten reagent on these types of systems. In addition, even if read times were available, use of the measured absorbance at the time of delivery would not accurately measure the delivery of the R2 polyhapten reagent, because it would contain interference signals from mixing and the agglutination reaction due to the presence of sample and antibody already present in the reaction mixture.

Further, no solutions are currently available for detecting issues with delivery of a reagent that also starts assay signal generation.

Therefore, there is a need in the art for new and improved methods to isolate absorbance solely attributed to addition of an assay reagent, and in particular (but not by way of limitation), to new and improved methods of detecting and flagging issues caused by R2 polyhapten reagent delivery. It is to such new and improved methods, as well as devices and compositions used therein, that the present disclosure is directed.

DETAILED DESCRIPTION

Figure 1:
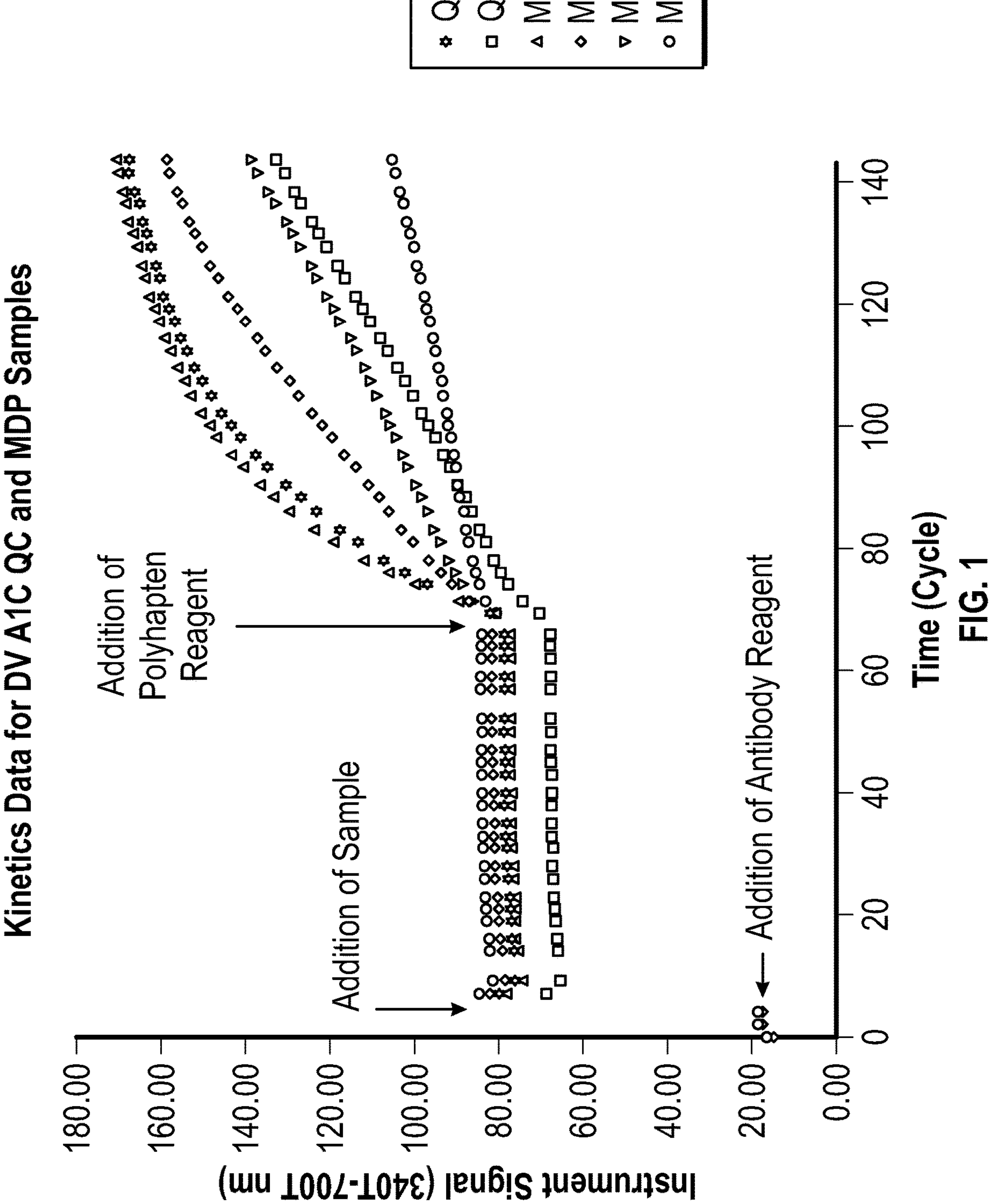
FIG. 1 graphically depicts kinetics data for an A1C assay using quality control (QC) and Medical Decision Pool (MDP) samples.

Before explaining at least one embodiment of the inventive concepts in detail by way of exemplary language and results, it is to be understood that the inventive concepts are not limited in their application to the details of construction and the arrangement of the components set forth in the following description. The inventive concepts are capable of other embodiments or of being practiced or carried out in various ways. As such, the language used herein is intended to be given the broadest possible scope and meaning, and the embodiments are meant to be exemplary—not exhaustive. Also, it is to be understood that the phraseology and terminology employed herein is for the purpose of description only and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the inventive concepts as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety, and coating one moiety on another moiety, for example.

The term "sample" as used herein will be understood to include any type of biological sample that may be utilized in accordance with the present disclosure. Examples of fluidic biological samples that may be utilized include, but are not limited to, whole blood or any portion thereof (including, but not limited to, plasma or serum), whole or lysed blood cells (including, but not limited to, whole or lysed red blood cells), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "target analyte-specific binding partner" as used herein will be understood to refer to any molecule capable of specifically associating with the target analyte. For example but not by way of limitation, the binding partner may be an antibody, a receptor, a ligand, aptamers, molecular imprinted polymers (i.e., inorganic matrices), combinations or derivatives thereof, as well as any other molecules capable of specific binding to the target analyte.

The term "antibody" is used herein in the broadest sense and refers to, for example, intact monoclonal antibodies and polyclonal antibodies, multi-specific antibodies (e.g., bispecific antibodies), antibody fragments and conjugates thereof that exhibit the desired biological activity of analyte binding (such as, but not limited to, Fab, Fab', F(ab')2, Fv, scFv, Fd, diabodies, single-chain antibodies, and other antibody fragments and conjugates thereof that retain at least a portion of the variable region of an intact antibody), antibody substitute proteins or peptides (i.e., engineered binding proteins/peptides), and combinations or derivatives thereof. The antibody can be of any type or class (e.g., IgG, IgE, IgM, IgD, and IgA) or sub-class (e.g., IgG1, IgG2, IgG3, IgG4, IgA1, and IgA2).

The term "hapten" as used herein refers to a small proteinaceous or non-protein antigenic determinant (or "epitope") which is capable of being recognized by a target analyte-specific binding partner, such as (but not limited to) an antibody. The term "polyhapten" as used herein will be understood to refer to a synthetic molecule that contains multiple epitopes/antigenic determinants attached thereto.

An "analyte" is a macromolecule that is capable of being recognized by a target analyte-specific binding partner, such as (but not limited to) an antibody. Both analytes and haptens comprise at least one antigenic determinant or "epitope," which is the region of the antigen or hapten which binds to the target analyte-specific binding partner (i.e., antibody). Typically, the epitope on a hapten is the entire molecule.

The term "reaction cuvette" as used herein includes any device(s) capable of performing at least one diagnostic assay as described herein. The reaction cuvette may perform the diagnostic assay(s) manually, but, in most instances, the reaction cuvette will be inserted into a system that automates the performance of the diagnostic assay(s). In one non-limiting embodiment, the reaction cuvette comprises a reaction cuvette for use in automated diagnostic assays conducted by, for example but not by way of limitation, one of the DIMENSION VISTA® Systems commercially available from Siemens Healthcare Diagnostics, Inc. (Newark, DE). However, it will be understood that the reaction cuvette can be any commercially available product or cuvette described or otherwise contemplated herein that is capable of performing one or more diagnostic assays in accordance with the present disclosure.

The term "turbidimetry" as used herein will be understood to refer to a process of measuring the loss of intensity of transmitted light due to the scattering effect of particles suspended in a solution. Light passed through a filter creates a light of known wavelength, which is then passed through a cuvette containing the test solution. A photometer collects the light which passes through the cuvette, and a measurement is then given for the amount of absorbed light. Thus, turbidimetry is a method for determining the concentration of a substance in a solution by the degree of cloudiness or turbidity the substance causes or by the degree of clarification it induces in a turbid solution.

Turning now to the inventive concepts, certain non-limiting embodiments of the present disclosure relate generally to kits, devices, and methods for improving the performance and reliability of immunoassays. In particular, certain embodiments of the present disclosure are related to kits, devices, and methods for detecting delivery issues for polyhapten reagents.

As stated herein above, a major concern for HbA1c immunoassays involves delivery issues with the R2 polyhapten reagent, such as (but not limited to) short delivery or a broken air bubble, that cause aberrant results to be reported. R2 is a polypeptide solution that absorbs at 293 nm, a wavelength that is available on multiple clinical chemistry analyzers, such as (but not limited to) the DIMENSION VISTA® Systems (Siemens Healthcare Diagnostics Inc., Tarrytown, NY); however, there are no available read times immediately after the addition of the polyhapten reagent on these types of systems. In addition, even if read times were available, use of the measured absorbance at the time of delivery would not accurately measure the delivery of the R2 polyhapten reagent, because it would contain interference signals from mixing and the agglutination reaction due to the presence of sample and antibody already present in the reaction mixture.

Because of the above reasons, the approach of the present disclosure was developed to extrapolate the absorbance change (293 nm-700 nm) due to R2 delivery, using the slope of the regression line from two later reads versus time. This approach allows one to predict mAU absorbance of the R2 delivery at the time point immediately before the start of the agglutination reaction. The approach works because the absorbance change versus time is linear for the time points used and the predicted R2 delivery mAU signals for all HbA1c concentrations converge.

This approach of detecting issues with a reagent delivery that also triggers assay signal generation can be applied to any chemistry assay or immunoassay. Therefore, the description of this approach in the context of a polyhapten reagent in an HbA1c immunoassay is for purposes of illustration only and should not be construed as limiting.

In the methods of the present disclosure, calculations were added to the assay parameters to extrapolate the instrument signal at the time of delivery of the polyhapten reagent. This approach uses the regression of two later reads versus time to predict the signal at time 0 and subtracts the signal contribution from sample and antibody reagent in the reaction mixture in order to provide a true monitor of the signal from the addition of polyhapten reagent into the reaction. By removing the signal contribution from sample and antibody reagent, the instrument software is able to compare the signal from the polyhapten reagent delivery for each test and flag tests that were impacted by an issue with reagent delivery. This approach is effective because the change in signal versus time is linear for the time points used.

Overall, the novelty of this approach is to use zero-order reads to isolate out the absorbance resulted solely from a reagent delivery in the presence of other reaction signals. The calculations to monitor the delivery of polyhapten reagent provide the basis for a result monitor for this reagent delivery. If a gross error occurs during the delivery of this reagent, the error could have a clinically significant impact on patient results. The addition of this result monitor allows the instrument software to flag results that may be impacted by an issue with the delivery of the polyhapten reagent by the reagent 2 probe. The calculations added to the assay parameters monitor the consistency of the polyhapten reagent delivery and can detect issues with the delivery. The extrapolation is possible because the change in signal versus time is linear. As such, the methods of the present disclosure prevent the user from reporting a result that could have been impacted by a polyhapten delivery issue.

There are multiple advantages provided by the methods of the present disclosure (referred to at certain points herein as a "Reagent Delivery Check"). If patient results are impacted by an issue with the delivery of a reagent (such as, but not limited to, the R2 polyhapten reagent) and then reported to a physician, the physician may 1) question the result or 2) adjust treatment of the patient based on the result. In addition, this result monitor will not only flag results that may have been impacted by a delivery issue with the polyhapten reagent, but will also provide guidance to service personnel for more efficient troubleshooting in resolving a potential instrument issue. When this result monitor is triggered, service personnel can focus on specific reagent wells in a reagent cartridge and the reagent 2 system on the instrument instead of running service methods for all components of the instrument. This could reduce the time and cost for resolving an instrument issue (such as the cost of replacing parts for other components on the sample and reagent servers).

Certain non-limiting embodiments of the present disclosure are directed to methods for detecting the presence and/or concentration of a target analyte in a biological sample. In certain particular (but non-limiting) embodiments, the methods may be further defined as methods of minimizing aberrant or incomplete results in immunoassays caused by incomplete delivery of an immunoassay reagent (such as, but not limited to, a polyhapten reagent).

The methods include combining, either simultaneously or wholly or partially sequentially: (1) a biological sample suspected of containing the target analyte; (2) at least one target analyte-specific binding partner (such as, but not limited to, an antibody); and (3) at least one immunoassay reagent capable of specifically binding to the target analyte-specific binding partner (such as, but not limited to, a polyhapten reagent or other type of particle agglutination assay reagent). The at least one target analyte-specific binding partner is then allowed to bind to the target analyte or the at least one immunoassay reagent.

In certain non-limiting embodiments, the signal generated by the immunoassay reagent may be detected via a turbidimetric (i.e., an agglutination) assay. These types of assays are well known in the art, and therefore no further description thereof is deemed necessary.

Any target peptide or protein analytes capable of detection via immunoassays may be detected via the methods of the present disclosure. Examples of target analytes include, but are not limited to, glycated hemoglobin (HbA1c), albumin, human chorionic gonadotropin (hCG), ferritin, growth hormone, prolactin, thyroglobulin (Tg), C-reactive protein (CRP), Rheumatoid Factor (RF), and the like.

Alternatively, the immunoassay may be a therapeutic drug monitoring (TDM) immunoassay that measures the serum level of a drug to ensure its concentration is within a therapeutic range therefor. Examples of target drug analytes capable of detection via TDM immunoassays include, but are not limited to, gentamicin, tobramycin, CRP, digoxin, amikacin, caffeine, carbamazepine, digitoxin, disopyramide, ethosuxamide, lidocaine, lithium methotrexate, NAPA, phenobarbital, phenytoin, primidone, procainamide, quinidine, theophylline, tobramycin, valproic acid, vancomycin, and the like.

Any biological sample known in the art for use with immunoassays as described herein may be utilized in accordance with the present disclosure. Examples of biological samples that may be utilized include, but are not limited to, urine, whole blood or any portion thereof (including, but not limited to, plasma or serum), whole (i.e., substantially unlysed) or lysed blood cells (including, but not limited to, whole or lysed red blood cells), saliva, sputum, cerebrospinal fluid (CSF), intestinal fluid, intraperitoneal fluid, cystic fluid, sweat, interstitial fluid, tears, mucus, bladder wash, semen, combinations thereof, and the like.

In certain non-limiting embodiments, the present disclosure is directed to a method of detecting aberrant results caused by incomplete delivery of a polyhapten reagent used in an immunoassay. The method includes the following steps: (A) reacting, within a reaction cuvette, a biological sample suspected of containing a target analyte with a target analyte-specific binding partner, thereby forming a soluble analyte/specific binding partner complex; (B) adding a polyhapten reagent to the reaction cuvette, wherein the polyhapten reagent reacts with excess target analyte-specific binding partner to form an insoluble polyhapten/target analyte-specific binding partner complex; (C) irradiating the reaction cuvette with light; (D) measuring absorbance values at multiple time points at at least three wavelengths following addition of the polyhapten reagent, wherein a first wavelength turbidimetrically detects the insoluble polyhapten/target analyte-specific binding partner complex, a second wavelength detects protein, and a third wavelength serves as a blank; (E) extrapolating an absorbance value for the polyhapten reagent at the time of delivery thereof using a regression of absorbance values measured at the second and third wavelengths at two time points following addition of the polyhapten reagent; and (F) flagging, as unacceptable, a concentration value for the target analyte obtained by a separate algorithm if the extrapolated absorbance value for the polyhapten reagent at the time of delivery thereof varies from a predicted value therefor by more than an established flag constant.

Any target analytes described or otherwise contemplated herein may be detected by the methods described herein. In certain particular (but non-limiting) embodiments of any of the above methods, the analyte is HbA1c, the antibody is an anti-HbA1c antibody, and the polyhapten comprises a plurality of an HbA1c epitope.

In certain non-limiting embodiments, the present disclosure is directed to a method of detecting aberrant results caused by incomplete delivery of a polyhapten reagent used in a glycated hemoglobin (HbA1c) immunoassay. The method includes the following steps: (A) reacting, within a reaction cuvette, a biological sample suspected of containing a target analyte comprising HbA1c with an anti-HbA1c antibody to the target analyte, thereby forming a soluble HbA1c-antibody complex; (B) adding a polyhapten reagent to the reaction cuvette, wherein the polyhapten reagent reacts with excess anti-HbA1c antibody to form an insoluble polyhapten/target analyte-specific binding partner complex; (C) irradiating the reaction cuvette with light; (D) measuring absorbance values at multiple time points at at least three wavelengths following addition of the polyhapten reagent, wherein a first wavelength turbidimetrically detects the insoluble polyhapten/target analyte-specific binding partner complex, a second wavelength detects protein, and a third wavelength serves as a blank; (E) extrapolating an absorbance value for the polyhapten reagent at the time of delivery thereof using a regression of absorbance values measured at the second and third wavelengths at two time points following addition of the polyhapten reagent; and (F) flagging, as unacceptable, a concentration value for the target analyte obtained by a separate algorithm if the extrapolated absorbance value for the polyhapten reagent at the time of delivery thereof varies from a predicted value therefor by more than an established flag constant.

Any of the methods described or otherwise contemplated herein may further include the steps of lysing a biological sample in a first vessel/cuvette and then transferring the lysed biological sample to the reaction cuvette utilized in step (A).

Any wavelengths may be utilized as the first, second, and third wavelengths in accordance with any of the methods of the present disclosure, so long as the values described herein can be determined at such wavelengths. For example, any wavelength may be utilized as the first wavelength so long as the wavelength can detect the presence of protein/peptide and thus can detect reagent delivery and thereby provide an indication of the aggregation state of the polyhapten (or any other type of protein/polypeptide). Likewise, any wavelength may be utilized as the second wavelength so long as there is at least a minimal effect caused by the hapten that can be observed at this wavelength. In addition, any wavelength may be utilized as the third wavelength so long as there is minimal protein/peptide detection at that wavelength such that the third wavelength can serve as a "blanking wavelength" or "control wavelength" (i.e., a wavelength at which absorbance does not change as much as the first and second wavelengths) that ensures that the measurements obtained at the second wavelength are reliable and reproducible.

In certain non-limiting embodiments, the first wavelength is in a range of from about 300 nm to about 650 nm, the second wavelength is in a range of from about 190 nm to about 300 nm, and the third wavelength is in a range of from about 650 nm to about 850 nm. In a particular (but non-limiting) embodiment, the first wavelength is about 340 nm, the second wavelength is about 293 nm, and the third wavelength is about 700 nm.

In certain particular (but non-limiting) embodiments, the absorbance at the first wavelength is a bichromatic value calculated as a first change in absorbance defined as $(mAU_{first\ wavelength}-mAU_{third\ wavelength})$, and the absorbance at the second wavelength is a bichromatic value calculated as a second change in absorbance defined as $(mAU_{second\ wavelength}-mAU_{third\ wavelength})$. Any wavelength that will serve as a "blanking wavelength" and allow for calculation of the bichromatic values described or otherwise contemplated herein can be utilized as the third wavelength in accordance with the present disclosure. Non-limiting examples of wavelengths that may be utilized as the third wavelength include those in a range of from about 650 nm to about 850 nm, including (but not limited to) about 600 nm, about 650 nm, about 700 nm, about 750 nm, about 800 nm, and about 850 nm.

Any suitable regression analysis may be employed as the established regression in step (E) of the methods disclosed or otherwise contemplated herein. Non-limiting examples of regression analyses that can be utilized include linear regressions as well as non-linear regressions such as (but not limited to) logarithmic curves, exponential curves, hyperbolic curves, parabolic curves, sigmoidal curves, Michaelis Menten curves, polynomial curves, logistic regression (or logit) curves, and the like.

In a particular (but non-limiting) embodiment, the established flag constant utilized in step (F) is determined as follows. A running mean value is calculated for A1C tests, and the mean is based on values from a minimum of (for example, but not by way of limitation) 50 tests and a maximum of (for example, but not by way of limitation) 500 tests. Once the mean has been established using a minimum of 50 values, the results monitor is 'turned on' and actively compares new values from A1C tests to the results monitor range around the mean. The running mean includes a minimum of 50 values and a maximum of 500 values. When more than 500 values have been collected for the results monitor, values are replaced on a 'first in, first out' basis. As a result, the older values are removed from the mean, and newer values are added to the mean so that a total of 500 values are used. Each lot has its own running mean value and range based on pre-established criteria. In Example 2 described herein after, the pre-established criteria (i.e., "established flag constants") for the range were 12% above the mean and 15% below the mean.

As stated above, for the A1C assay, the acceptable range for the results monitor values is based on an allowable percent (%) above and below the mean. A measured value is compared to the acceptable range around the mean. If a value is within this range, then that value is added into the running mean calculation. If a value is outside the range, the value is not added into the running mean calculation, and the A1C assay result is accompanied by an 'abnormal assay' flag which alerts the user that the result is not valid and should not be reported.

The term "established flag constant" as used herein refers to a value that is a cut-off beyond which a significant difference between the measured and predicted value is observed. The established flag constant represents a value that exceeds an acceptable variation margin/range for an absorbance obtained for a sample, based upon the sample's measured values when compared to the values predicted therefor from the regression analysis. The established flag constant may be any arbitrary numerical value that indicates the upper end of the acceptable variation margin/range, such as, but not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 6, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, and the like, or any non-integer value therebetween, or any negative value thereof (i.e., −5, −65, etc.), or any slight variation in any of the values listed above (i.e., "about 11," about −15," etc.). Alternatively, the established flag constant may be a percentage that indicates the upper end of the acceptable variation margin/range, such as, but not limited to, 5000%, 4000%, 3000%, 2000%, 1000%, 900%, 800%, 700%, 600%, 500%, 450%, 400%, 350%, 300%, 250%, 200%, 150%, 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12% 11% 10% 9% 8% 7% 6% 5% 4% 3% 2% 1% and the like or any integer or non-integer percentage value therebetween, or any negative value thereof (i.e., −15%, −12%, etc.), or any slight variation in any of the percentage values listed above (i.e., "about 85%," about −15%," etc.).

In certain non-limiting embodiments, the measurements obtained in the methods of detecting aberrant results described or otherwise contemplated herein are measured and calculated independent of the actual assay for target analyte presence and/or concentration in the biological sample. Alternatively, one or more of the measurements obtained by the methods described and/or contemplated herein may be utilized in the actual assays for target analyte presence and/or concentration in the biological sample.

In certain non-limiting embodiments, when one or more values is flagged in step (F), the method may further comprise the step of instructing a user to repeat the assay steps (A)-(F).

It will be understood that, while the methods are described herein above for use with a polyhapten reagent, the methods of detecting aberrant results of the present disclosure are also applicable to use with other types of incompletely delivered particle agglutination assay reagents. Therefore, the scope of the present disclosure further includes any and all variations of the methods described herein above where the term "polyhapten reagent" is replaced with "particle agglutination assay reagent."

Any of the method steps described herein may be performed, for example but not by way of limitation, by a user. However, as used herein, the term "user" is not limited to use by a human being; rather, the term "user" may comprise (for example, but not by way of limitation) a computer, a server, a website, a processor, a network interface, a human, a user terminal, a virtual computer, combinations thereof, and the like.

The various embodiments of the present disclosure may be utilized with any reflectance spectroscopic diagnostic instrument that is capable of (or has been modified to be capable of) functioning in accordance with the methods described herein. In certain, non-limiting embodiments, the instrument may be a point of care instrument. The reflectance spectroscopic diagnostic instrument may be a system or systems that are able to embody and/or execute the logic of the methods/processes described herein. Logic embodied in the form of software instructions and/or firmware may be executed on any appropriate hardware. For example, logic embodied in the form of software instructions and/or firmware may be executed by one or more components on a dedicated system or systems, on a personal computer system, on a distributed processing computer system, and/or the like. In some embodiments, the entire logic may be implemented in a stand-alone environment operating on an instrument (such as, but not limited to, a point of care instrument). In other embodiments, the logic may be implemented in a networked environment such as a distributed system in which multiple instruments collect data that is transmitted to a centralized computer system for analyzing the data and supplying the results of the analysis to the instruments. Each element of the instrument may be partially or completely network-based or cloud based, and may or may not be located in a single physical location.

Circuitry used herein includes (but is not limited to) analog and/or digital components, or one or more suitably programmed processors (e.g., microprocessors) and associated hardware and software, or hardwired logic. Also, "components" may perform one or more functions. The term "component" may include hardware, such as but not limited to, a processor (e.g., microprocessor), an application specific integrated circuit (ASIC), field programmable gate array (FPGA), a combination of hardware and software, and/or the like.

Software utilized herein may include one or more computer readable medium (i.e., computer readable instructions) that when executed by one or more components cause the component to perform a specified function. It should be understood that the algorithms described herein may be stored on one or more non-transient memory. Non-limiting exemplary non-transient memory may include random access memory, read only memory, flash memory, and/or the like. Such non-transient memory may be electrically based, optically based, and/or the like.

Certain non-limiting embodiments of the present disclosure are directed to reagent kits useful for conveniently performing the immunoassay methods described herein above. The reagent kit includes at least one target-analyte specific binding partner (such as, but not limited to, an antibody against the target analyte) and at least one polyhapten reagent, each as described in detail herein above.

Certain other non-limiting embodiments of the present disclosure are directed to an immunoassay device (such as, but not limited to, an immunoassay cartridge) which contain the reagent kits described herein above and which are for use in the immunoassay methods described herein above. For example, the immunoassay device may include at least one compartment capable of receiving a sample suspected of containing the target peptide or protein analyte, wherein the at least one compartment includes at least one target analyte-specific binding partner (such as, but not limited to, an antibody against the target analyte) as described in detail herein above and at least one polyhapten reagent as described in detail herein above.

In addition, the reagent kits and/or immunoassay devices of the present disclosure may further contain other component(s) and/or reagent(s) for conducting any of the particular immunoassays described or otherwise contemplated herein. The nature of these additional component(s)/reagent(s) will depend upon the particular immunoassay format, and identification thereof is well within the skill of one of ordinary skill in the art. Examples of additional reagents/components that may be present in the reagent kits and/or immunoassay devices of the present disclosure include, but are not limited to, diluents, lysing agents (for lysing red blood cells), wash solutions (such as but not limited to, isotonic solutions), positive controls, negative controls, quality controls, and/or actuators, as well as any combination thereof.

The relative amounts of the various components/reagents in the kits and/or immunoassay devices can vary widely to provide for concentrations of the components/reagents that substantially optimize the reactions that need to occur during the assay methods and further to optimize substantially the sensitivity of an assay.

The reagent kits of the present disclosure may further include a set of written instructions explaining how to use the kit. A kit of this nature can be used with any of the immunoassay devices and/or in any of the methods described or otherwise contemplated herein.

The immunoassay device may have one or more manual functions associated therewith (i.e., wherein pipetting is required for addition of one or more reagents and/or movement of a mixture between two compartments); alternatively, the immunoassay device may be a fully automatic, closed system in which the necessary reagents/components are disposed in various compartments during construction of the immunoassay device (wherein the various compartments are in continuous fluidic communication (or are capable of being in continuous fluidic communication)), and thus no manual manipulation of the sample and/or reagent(s) is required for performance of the assay after the sample is added to the immunoassay device.

The immunoassay device comprises one or more compartments containing the components/reagents described herein above; the immunoassay device may be provided with any number of compartments, any arrangement of compartments, and any distribution of the components/ reagents therebetween, so long as the device is able to function in accordance with the present disclosure. When provided with multiple compartments, the compartments may be completely separated from one another, or one or more compartments may be capable of being in fluidic communication with one another. Various structures of immunoassay devices that are capable of use in accordance with the present disclosure are well known in the art, and therefore no further description thereof is deemed necessary.

In certain embodiments, the immunoassay device includes at least first and second compartments. The first compartment is capable of receiving a biological sample and, if desired (but not by way of limitation), may include a mechanism for separating protein/peptide from the bulk of the sample, lysing red blood cells, etc. Said separation mechanisms are well known in the art of immunoassay devices, and therefore no further description thereof is deemed necessary. The second compartment is capable of being in fluidic communication with the first compartment and includes the at least one target analyte-specific binding partner (such as, but not limited to, an antibody against the target analyte) and/or the at least one immunoassay reagent for performing the immunoassay methods described in detail herein above. Alternatively, the immunoassay device may include a third compartment for storage of the at least one immunoassay reagent, and wherein the at least one immunoassay reagent can be transferred from the third compartment into the second compartment.

The immunoassay device may also include an optical read chamber that is capable of being optically interrogated by a spectrometer. The optical read chamber may be associated with any of the compartments described herein above, or the optical read chamber may be associated with a separate compartment from those described herein above.

The inlet channel and a compartment, as well as two compartments, may be described as being "capable of being in fluidic communication" with one another; this phrase indicates that the compartment(s) may still be sealed, but the two compartments are capable of having fluid flow therebetween upon puncture of a seal formed therein or therebetween.

The kits/immunoassay devices of the present disclosure may be provided with any other desired features known in the art or otherwise contemplated herein. For example, but not by way of limitation, the kits/immunoassay devices of the present disclosure may further include one or more additional compartments containing other solutions, such as but not limited to, lysing agents (for lysing red blood cells), diluents, wash solutions, labeling agents, interference solutions, positive controls, negative controls, quality controls, and/or actuators, as well as any combination thereof.

EXAMPLES

Examples are provided hereinbelow. However, the present disclosure is to be understood to not be limited in its application to the specific experimentation, results, and laboratory procedures disclosed herein. Rather, these Examples are simply provided as one of various embodiments and are meant to be exemplary, not exhaustive.

Example 1

R2 Polyhapten Delivery Check Result Monitor Procedure

The purpose of the R2 Polyhapten Delivery Check Result Monitor is to detect polyhapten delivery issues, which could include short delivery or a broken air bubble. Because the agglutination starts at the time of polyhapten delivery in the reaction mixture, and because there is no photometric read taken right after delivery, its delivery cannot be directly measured using mAU (293 nm-700 nm). Therefore, an approach to extrapolate the mAU (293 nm-700 nm) at the time of delivery (i.e., time 0 mAU right after the delivery and right before the agglutination reaction starts) was developed. This approach uses the regression of two later reads versus time to predict the time 0 mAU (see Example 2). The approach works because the change in signal versus time is linear for the time period used.

In order to monitor the delivery of the polyhapten reagent by the reagent 2 (R2) probe, a result monitor was added to the A1C sample assay parameters. The calculations for this result monitor were also added to the A1CC calibration assay parameters, but the result monitor code was not added.

Calculation approach for R2 polyhapten delivery check result monitor:

- In the assay parameters, the R2 probe adds polyhapten reagent at cycle 67.
- The R2 polyhapten reagent cannot be seen in the reaction until a time in between cycles 67 and 68 (referred to as "cycle 67+").
  - The time for "cycle 67+" was estimated to be [cycle 69—5.7 seconds].
  - Each cycle is 3.6 seconds.
- The R2 polyhapten reagent can be detected using the 293 nm wavelength and the 700 nm wavelength for blanking.
- The good reads for 293 nm and 700 nm before cycle 67 are cycles 52, 57, and 64.
  - The sample is transferred from the loci vessel to the cuvette at cycle 6, so the sample is present in the reaction at cycles 52, 57, and 64.
- The good reads for 293 nm and 700 nm after cycle 67 are cycles 69 and 71.
- The polyhapten absorbance after delivery (time 0 mAU) is calculated as follows:

Slope (cycles 69-71)*(time at cycle 67+)+(*Y*-intercept at time 0)

- The R2 polyhapten delivery check is calculated as follows:

(Polyhapten absorbance at cycle 67+)−(average absorbance at cycles 52, 57, 64).

Example 2

These calculations were done offline using photometer data collected during verification studies for the A1C assay. The data collected during verification studies did not show any evidence of issues related to the R2 delivery of polyhapten reagent. As a result, the assay parameters were modified to simulate different instrument issues that could occur during the delivery step.

In order to simulate different types of delivery issues, modifications were made to the A1C assay parameters in the manner indicated below (as well as in Table 1):

- Rg21: short delivery of polyhapten reagent with additional chase volume to keep reaction volume constant;
- Rg22: short delivery of polyhapten reagent with additional chase volume (to keep reaction volume constant) and removed air bubble;
- Rg23: short delivery of the polyhapten reagent—no additional chase (true short delivery);

Rg24: standard delivery from A1C parameters (28 μL) and removed air bubble;

Rg25: standard delivery from A1C parameters (28 μl), removed air bubble, and increased chase from 15 μl to 25 μl water; and Rg26: standard delivery from A1C parameters (28 μL), removed air bubble, and increased chase from 15 μl to 20 μl water.

Thus, each of Rg21-Rg26 mimic one or more delivery issues with the R2 reagent.

TABLE 1

Assay Parameters Created for R2 Polyhapten Reagent Delivery Studies

| Assay Parameters | Polyhapten Volume (μl) | Air Bubble Volume (μl) | Chase Volume (μl) |
|---|---|---|---|
| A1C | 28 | 10 | 15 |
| Rg21 | 14 | 10 | 29 |
| Rg22 | 14 | 0 | 29 |
| Rg23 | 14 | 10 | 15 |
| Rg24 | 28 | 0 | 15 |
| Rg25 | 28 | 0 | 25 |
| Rg26 | 28 | 0 | 20 |

For each set of assay parameters, the following samples were tested: Diabetes Control Levels 1 and 2 from LYPHO-CHEK® Diabetes Control (Bio-Rad Laboratories, Inc., Hercules, CA) and Medical Decision Pools (MDP) 1-4. All MDP were tested n=5, and quality control (QC) samples were tested n=2 or n=5, depending on the study. For each assay parameter study, the impact to % HbA1c results was calculated as well as the change in the R2 polyhapten delivery check values.

FIG. 1 illustrates the kinetics data for DV A1C for QC and MDP samples. As can be seen, a small amount of absorbance is seen at the beginning of the assay, and this absorbance corresponds to addition of the antibody reagent. Upon addition of sample at cycle 6 an increase in absorbance is seen. Following addition of the polyhapten reagent at cycle 67, the absorbance immediately begins to increase in response to the agglutination reaction between free antibody and polyhapten.

The measurement of HbA1c in the reaction is based on the agglutination of free antibody with polyhapten:

When more HbA1c is present in the reaction, then more antibody is bound to HbA1c, and so less antibody is available to agglutinate with polyhapten. Less agglutination between the antibody and polyhapten results in a lower HbA1c signal, which leads to a higher HbA1c analyte result.

When less HbA1c is present in the reaction, then less antibody is bound to HbA1c, and more antibody is available to agglutinate with polyhapten. More agglutination between the antibody and polyhapten results in a higher HbA1c signal, which leads to a lower HbA1c analyte result.

Figure 2:
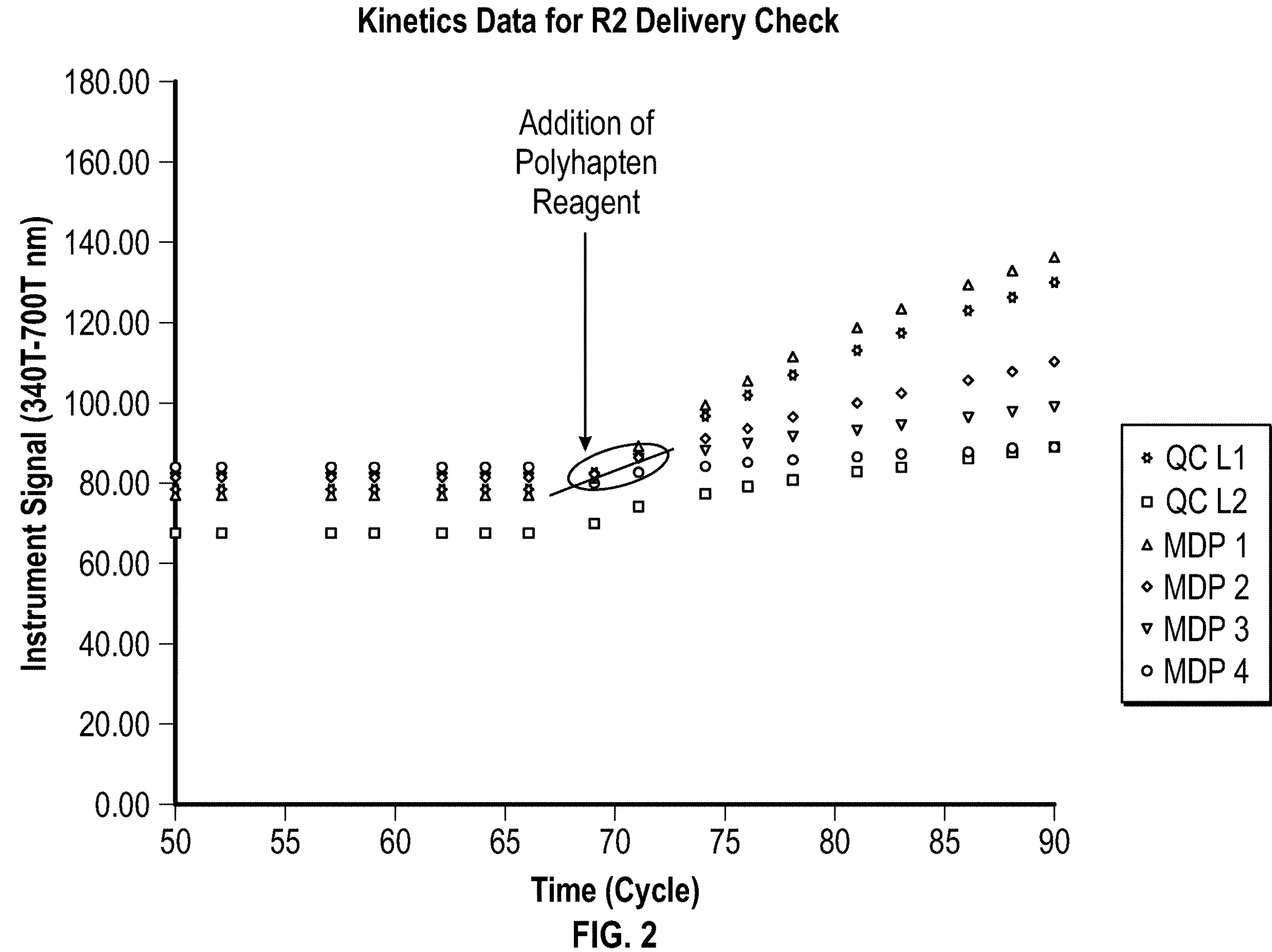
FIG. 2 graphically depicts kinetics data for an R2 polyhapten delivery check assay constructed in accordance with the present disclosure.

FIG. 2 indicates how the polyhapten delivery check monitor is performed. Upon addition of the polyhapten reagent at cycle 67, reads are obtained immediately thereafter at cycles 69 and 71, and then these two reads are utilized to linearly extrapolate out a time 0 mAU value for the polyhapten reagent (see circled linear extrapolation).

The first study compared the control parameters (A1C1 was a clone of the A1C parameters) to Rg21 and Rg22 parameters, which had a reduced delivery volume of polyhapten reagent with an increased chase volume. The data from this study is shown in Table 2.

TABLE 2

Data from Comparison of A1C1, Rg21, and Rg22

| Sample | Methpar | Mean R2 Poly Deliv Check | % HbA1c | % Difference from Control – Analyte (% HbA1c) | % Difference from Control – Mean R2 Poly Deliv Check |
|---|---|---|---|---|---|
| QC 33941 | A1C1 | 157 | 5.3 | — | — |
| QC 33941 | Rg21 | 113 | 6.4 | 19.8 | −28.0 |
| QC 33941 | Rg22 | 111 | 6.1 | 15.1 | −29.3 |
| QC 33942 | A1C1 | 154 | 9.2 | — | — |
| QC 33942 | Rg21 | 117 | 10.0 | 8.7 | −23.8 |
| QC 33942 | Rg22 | 112 | 10.0 | 8.7 | −27.0 |
| MDP1 | A1C1 | 155 | 5.1 | — | — |
| MDP1 | Rg21 | 114 | 5.7 | 13.4 | −26.3 |
| MDP1 | Rg22 | 112 | 5.6 | 11.1 | −27.5 |
| MDP2 | A1C1 | 156 | 6.4 | — | — |
| MDP2 | Rg21 | 113 | 7.2 | 12.1 | −27.4 |
| MDP2 | Rg22 | 111 | 7.2 | 12.4 | −28.5 |
| MDP3 | A1C1 | 155 | 7.9 | — | — |
| MDP3 | Rg21 | 118 | 8.3 | 5.9 | −24.2 |
| MDP3 | Rg22 | 112 | 8.4 | 6.6 | −27.6 |
| MDP4 | A1C1 | 156 | 11.7 | — | — |
| MDP4 | Rg21 | 115 | 11.8 | 1.0 | −25.9 |
| MDP4 | Rg22 | 110 | 11.8 | 1.4 | −29.1 |
| QC 33941 | A1C1 | 157 | 5.4 | — | — |
| QC 33941 | Rg21 | 113 | 6.4 | 17.6 | −28.1 |
| QC 33941 | Rg22 | 110 | 6.2 | 14.8 | −29.9 |
| QC 33942 | A1C1 | 158 | 9.5 | — | — |
| QC 33942 | Rg21 | 114 | 10.1 | 6.9 | −27.7 |
| QC 33942 | Rg22 | 112 | 10.0 | 5.8 | −29.2 |

When the delivery of polyhapten reagent was reduced and replaced with water chase, the HbA1c signal was reduced, which led to higher HbA1c analyte results. Since the polyhapten addition occurs after hemoglobin is measured, the hemoglobin concentration was not impacted, and the increase in the HbA1c result elevated % HbA1c results. The values for the polyhapten delivery check in these parameters were lower than those from the control parameters.

The second study compared the control parameters to Rg23, Rg24, Rg25, and Rg26. These parameters were described in Table 1, and the data is shown in Table 3.

For the Rg25 and Rg26 parameters, the volume of polyhapten delivered was not modified, but the air bubble was removed and replaced with varying volumes of water chase. These parameters were created to simulate a delivery of polyhapten reagent in which the air bubble breaks and is partially or completely replaced by chase water. One would expect the HbA1c signal to be lower due to the dilution of the reaction mixture. This lower signal would lead to higher HbA1c analyte results. Since the reaction volume was not corrected in the calculations, the HbA1c signal was not reduced as much as expected. As a result, the signal was reduced compared to the control parameters, but not as much as expected. The HbA1c results for these parameters were elevated compared to the control parameters. This data is shown in Table 3. The values for the polyhapten delivery check in these parameters were lower than those from the control parameters.

For the Rg23 parameters, where the polyhapten volume was reduced by half, the presence of less polyhapten would be expected to lead to less agglutination, which would result in a lower HbA1c signal. A lower HbA1c signal would be expected to lead to a higher HbA1c analyte result. At the same time, the total volume of the reaction was reduced by 14 μl. This lower volume would lead to higher agglutination and a higher HbA1c signal, which would lead to a lower HbA1c analyte result. In this situation, the two factors (less polyhapten and lower reaction volume) will compete.

Discussion of Competing Factors:

For the Rg21 parameters, the % HbA1c result was increased by ˜0.8% HbA1c. For the Rg25 and Rg26 parameters, the % HbA1c result for Rg26 was ˜0.5% HbA1c lower than Rg25, which contained an additional 5 μL of water chase (depending on the % HbA1c level). The difference in polyhapten volume between Rg23 and the control parameters, A1C1, is 14 μL. This would lead one to expect a decrease in % HbA1c of ˜1.4% HbA1c. Because both effects are present in the Rg23 parameters, the results showed a decrease in % HbA1c. This decrease in results varied depending on the analyte level.

TABLE 3

Data from Comparison of A1C1, Rg23, Rg24, Rg25, and Rg26

| Sample | Details | Methpar | Mean R2 Blank @ Cycle 67 | % HbA1c | % Difference from Control − Analyte (% HbA1c) | % Difference from Control − Mean R2 Blank @ Cycle 67 |
|---|---|---|---|---|---|---|
| 33941 | BOR, QC, n = 2 | A1C1 | 157 | 5.3 | — | — |
| 33941 | BOR, QC, n = 2 | Rg23 | 181 | 5.1 | −3.8 | 15.2 |
| 33941 | BOR, QC, n = 2 | Rg24 | 155 | 5.4 | 1.9 | −1.3 |
| 33941 | BOR, QC, n = 2 | Rg25 | 114 | 5.7 | 8.6 | −27.5 |
| 33941 | BOR, QC, n = 2 | Rg26 | 136 | 5.5 | 4.8 | −13.4 |
| 33942 | BOR, QC, n = 2 | A1C1 | 156 | 9.2 | — | — |
| 33942 | BOR, QC, n = 2 | Rg23 | 180 | 8.9 | −3.3 | 15.2 |
| 33942 | BOR, QC, n = 2 | Rg24 | 154 | 9.1 | −1.1 | −1.2 |
| 33942 | BOR, QC, n = 2 | Rg25 | 114 | 9.9 | 7.7 | −27.3 |
| 33942 | BOR, QC, n = 2 | Rg26 | 133 | 9.5 | 3.3 | −15.1 |
| 33941 | EOR, QC, n = 2 | A1C1 | 157 | 5.4 | — | — |
| 33941 | EOR, QC, n = 2 | Rg23 | 181 | 5.2 | −3.7 | 15.4 |
| 33941 | EOR, QC, n = 2 | Rg24 | 158 | 5.3 | −0.9 | 0.7 |
| 33941 | EOR, QC, n = 2 | Rg25 | 116 | 5.8 | 8.4 | −26.0 |
| 33941 | EOR, QC, n = 2 | Rg26 | 137 | 5.6 | 4.7 | −12.8 |
| 33942 | EOR, QC, n = 2 | A1C1 | 157 | 9.2 | — | — |
| 33942 | EOR, QC, n = 2 | Rg23 | 179 | 8.8 | −4.3 | 13.9 |
| 33942 | EOR, QC, n = 2 | Rg24 | 155 | 9.1 | −1.6 | −1.7 |
| 33942 | EOR, QC, n = 2 | Rg25 | 116 | 9.9 | 7.6 | −26.3 |
| 33942 | EOR, QC, n = 2 | Rg26 | 133 | 9.4 | 2.2 | −15.2 |
| MDP1 1 | n = 5 | A1C1 | 156 | 5.0 | — | — |
| MDP1 2 | n = 5 | Rg23 | 181 | 4.9 | −1.2 | 16.7 |
| MDP1 3 | n = 5 | Rg24 | 156 | 5.0 | 0.0 | 0.3 |
| MDP1 4 | n = 5 | Rg25 | 116 | 5.5 | 10.1 | −25.4 |
| MDP1 5 | n = 5 | Rg26 | 136 | 5.2 | 4.4 | −12.6 |
| MDP2 1 | n = 5 | A1C1 | 156 | 6.4 | — | — |
| MDP2 2 | n = 5 | Rg23 | 180 | 5.8 | −8.8 | 15.5 |
| MDP2 3 | n = 5 | Rg24 | 155 | 6.4 | −0.3 | −0.5 |
| MDP2 4 | n = 5 | Rg25 | 112 | 6.8 | 6.9 | −27.8 |
| MDP2 5 | n = 5 | Rg26 | 135 | 6.5 | 2.2 | −13.5 |
| MDP3 1 | n = 5 | A1C1 | 155 | 7.8 | — | — |
| MDP3 2 | n = 5 | Rg23 | 180 | 7.3 | −5.9 | 16.1 |
| MDP3 3 | n = 5 | Rg24 | 152 | 7.6 | −2.1 | −1.8 |
| MDP3 4 | n = 5 | Rg25 | 112 | 8.5 | 8.7 | −27.8 |
| MDP3 5 | n = 5 | Rg26 | 133 | 8.0 | 3.1 | −14.5 |
| MDP4 1 | n = 5 | A1C1 | 155 | 11.6 | — | — |
| MDP4 2 | n = 5 | Rg23 | 178 | 10.4 | −10.3 | 15.0 |
| MDP4 3 | n = 5 | Rg24 | 151 | 11.6 | 0.0 | −2.5 |
| MDP4 4 | n = 5 | Rg25 | 110 | 12.6 | 8.8 | −29.3 |
| MDP4 5 | n = 5 | Rg26 | 130 | 12.1 | 4.1 | −16.3 |
| 33941 1 | n = 5 | A1C1 | 152 | 5.3 | — | — |
| 33941 2 | n = 5 | Rg23 | 179 | 5.1 | −3.8 | 17.8 |
| 33941 3 | n = 5 | Rg24 | 154 | 5.2 | −1.5 | 1.4 |
| 33941 4 | n = 5 | Rg25 | 109 | 5.8 | 8.3 | −28.6 |

TABLE 3-continued

Data from Comparison of A1C1, Rg23, Rg24, Rg25, and Rg26

| Sample | Details | Methpar | Mean R2 Blank @ Cycle 67 | % HbA1c | % Difference from Control − Analyte (% HbA1c) | % Difference from Control − Mean R2 Blank @ Cycle 67 |
|---|---|---|---|---|---|---|
| 33941 5 | n = 5 | Rg26 | 133 | 5.5 | 3.4 | −12.7 |
| 33942 1 | n = 5 | A1C1 | 156 | 9.2 | — | — |
| 33942 2 | n = 5 | Rg23 | 179 | 8.8 | −4.3 | 14.3 |
| 33942 3 | n = 5 | Rg24 | 155 | 9.1 | −1.5 | −0.9 |
| 33942 4 | n = 5 | Rg25 | 114 | 9.9 | 7.8 | −26.9 |
| 33942 5 | n = 5 | Rg26 | 136 | 9.5 | 3.0 | −13.2 |

Figure 3:
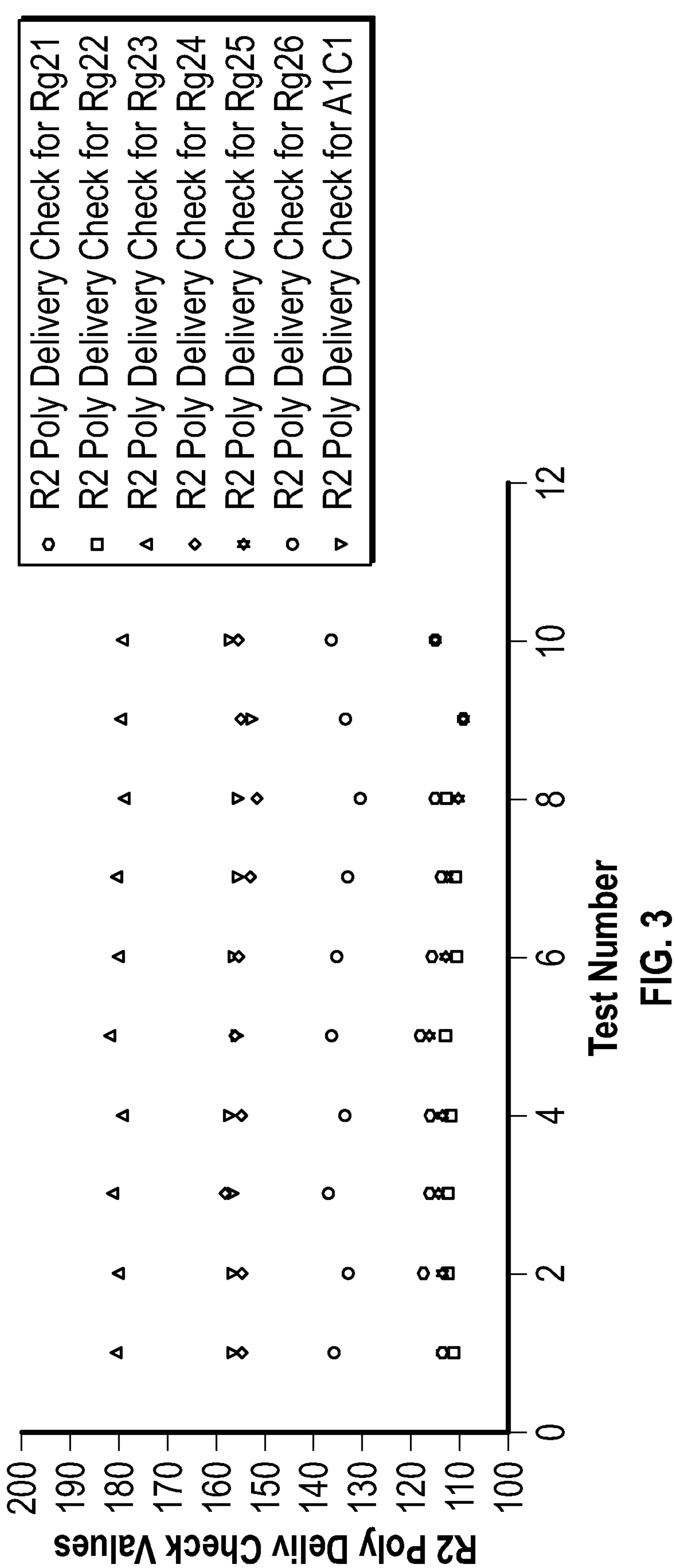
FIG. 3 graphically depicts R2 polyhapten delivery check data from assay parameters designed to simulate issues related to the delivery of polyhapten reagent.

FIG. 3 graphically depicts R2 polyhapten delivery check data from assay parameters designed to simulate issues related to the delivery of polyhapten reagent. Each data point represents a mean value calculated from 2-5 tests/replicates. Samples contained different HbA1c analyte levels (QC L1, QC L2, MDP 1-4).

Figure 4:
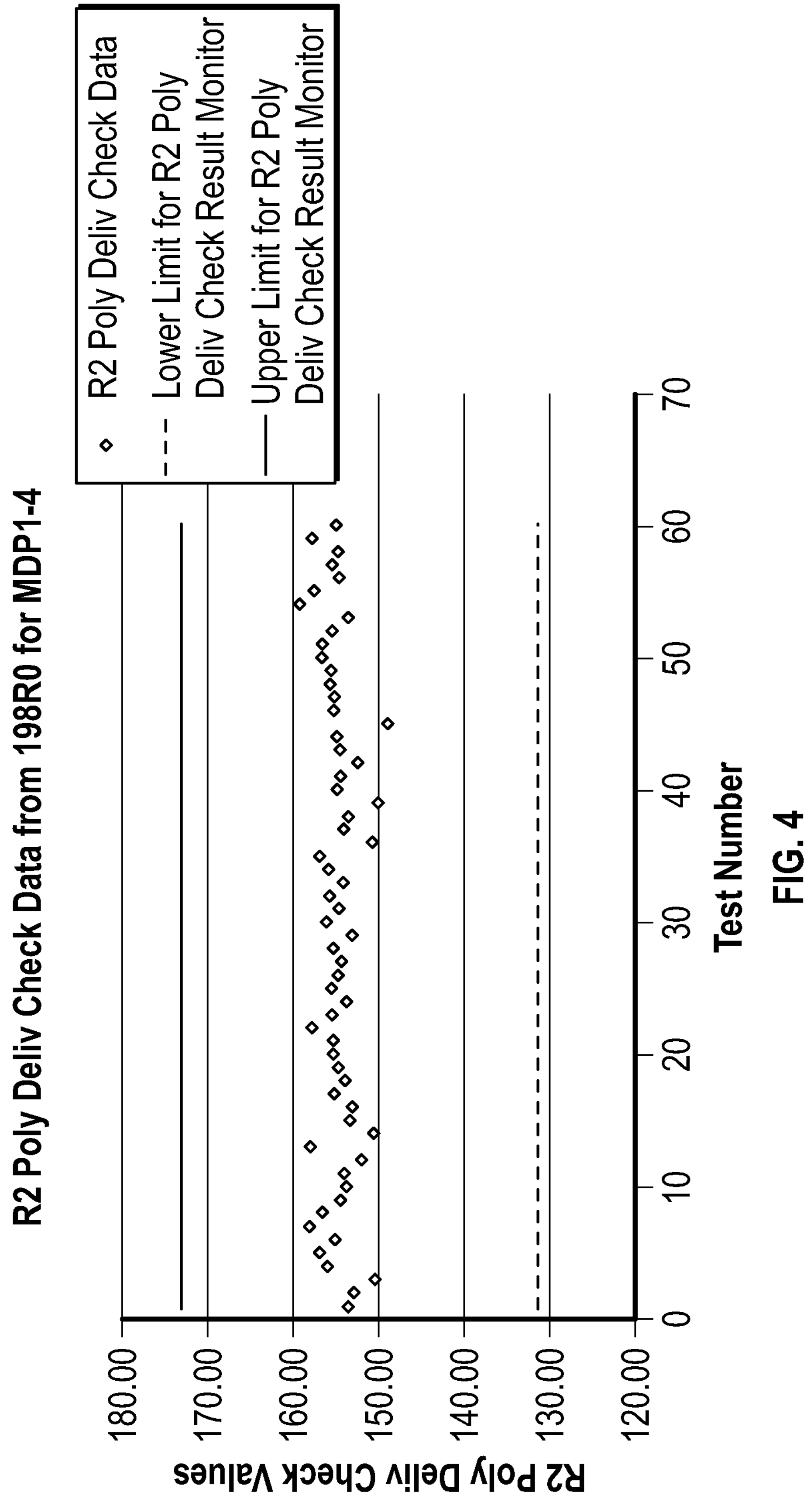
FIG. 4 graphically depicts R2 polyhapten delivery check data for samples compared to result monitor limits.

FIG. 4 graphically depicts R2 polyhapten delivery check data for samples compared to result monitor limits. Each data point represents a value calculated for an individual test. Samples were MDP 1-4, which contained different HbA1c analyte levels.

Based on the data from these two studies, the limits for the R2 polyhapten delivery check were set to −15% and +12% when compared to the mean value for this delivery check.

Conclusion: Based on the data from these studies, the limits (i.e., "established flag constants") of mean−15% and mean+12% for the R2 polyhapten delivery check were set in order to flag results that could see a clinically significant impact from an issue with the delivery of the polyhapten reagent.

However, these flag constants are established for purposes of example only and thus are non-limiting of the present disclosure; any other flag constant values calculated in accordance with the methods described or otherwise contemplated herein may also be utilized in accordance with the present disclosure and thus fall within the scope thereof.

Thus, in accordance with the present disclosure, there have been provided methods, as well as compositions, kits, and devices for use therein, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed inventive concepts.

What is claimed is:

1. A method of detecting aberrant results caused by incomplete delivery of a polyhapten reagent used in an inhibition immunoassay, the method comprising the steps of:

(A) inserting a reaction cuvette into a clinical chemistry analyzer system and reacting, within the reaction cuvette, a biological sample suspected of containing a target analyte with a target analyte-specific binding partner, thereby forming a soluble analyte/specific binding partner complex;

(B) adding a polyhapten reagent to the reaction cuvette, wherein the polyhapten reagent comprises multiple copies of an epitope of the target analyte to which the target analyte-specific binding partner binds, and wherein the polyhapten reagent reacts with excess target analyte-specific binding partner to form an insoluble polyhapten/target analyte-specific binding partner complex;

(C) irradiating the reaction cuvette with light at at least three wavelengths, wherein a first wavelength turbidimetrically detects the insoluble polyhapten/target analyte-specific binding partner complex, the second wavelength detects the polyhapten reagent, and the third wavelength serves as a blank, and wherein the first wavelength is about 340 nm, the second wavelength is about 293 nm, and the third wavelength is about 700 nm;

(D) measuring absorbance values at the first, second, and third wavelengths at at least two time points following a time of delivery of the polyhapten reagent, wherein absorbance values at the first wavelength provide an indication of a concentration value for the target analyte, absorbance values at the second wavelength provide an indication of the polyhapten reagent, and wherein there is minimal to no protein/peptide detection at the third wavelength;

(E) extrapolating an absorbance value for the polyhapten reagent at the time of delivery thereof using a regression of absorbance values measured at the second and third wavelengths at two time points following the time of delivery of the polyhapten reagent; and (F) reporting to a user that a concentration value for the target analyte obtained by a separate algorithm has been flagged as unacceptable if the extrapolated absorbance value for the polyhapten reagent at the time of delivery thereof varies from a predicted value therefor by more than an established flag constant, the established flag constant set in order to flag results that are significantly impacted by incomplete delivery of the polyhapten reagent.

2. The method of claim 1, wherein the target analyte is selected from the group consisting of glycated hemoglobin (HbA1c), albumin, human chorionic gonadotropin (hCG), ferritin, growth hormone, prolactin, thyroglobulin (Tg), C-reactive protein (CRP), Rheumatoid Factor (RF), gentamicin, tobramycin, CRP, digoxin, amikacin, caffeine, carbamazepine, digitoxin, disopyramide, ethosuxamide, lidocaine, lithium methotrexate, NAPA, phenobarbital, phenytoin, primidone, procainamide, quinidine, theophylline, tobramycin, valproic acid, and vancomycin.

3. The method of claim 1, wherein the target analyte-specific binding partner is an antibody against the target analyte.

4. The method of claim 3, wherein the target analyte is glycated hemoglobin (HbA1c), the target analyte-specific binding partner is an anti-HbA1c antibody, and the polyhapten reagent comprises a plurality of an HbA1c epitope.

5. The method of claim 1, wherein in step (E), the first of the two time points following addition of the polyhapten reagent is about 7.2 seconds following addition of the polyhapten reagent, and wherein the second of the two points is about 7.2 seconds after the first of the two time points.

6. The method of claim 1, wherein the biological sample is selected from the group consisting of urine, whole blood or any portion thereof, whole or lysed blood cells, saliva, sputum, cerebrospinal fluid, intestinal fluid, intraperitoneal fluid, cystic fluid, sweat, interstitial fluid, tears, mucus, bladder wash, semen, and combinations thereof.

7. A method of detecting aberrant results caused by incomplete delivery of a polyhapten reagent used in a glycated hemoglobin (HbA1c) inhibition immunoassay, the method comprising the steps of:

(A) inserting a reaction cuvette into a clinical chemistry analyzer system and reacting, within the reaction cuvette, a biological sample suspected of containing a target analyte comprising HbA1c with an anti-HbA1c antibody to the target analyte, thereby forming a soluble HbA1c-antibody complex;

(B) adding a polyhapten reagent to the reaction cuvette, wherein the polyhapten reagent comprises multiple copies of an epitope of HbA1c to which the anti-HbA1c antibody binds, and wherein the polyhapten reagent reacts with excess anti-HbA1c antibody to form an insoluble polyhapten/anti-HbA1c antibody complex;

(C) irradiating the reaction cuvette with light at at least three wavelengths, wherein a first wavelength turbidimetrically detects the insoluble polyhapten/anti-HbA1c complex, the second wavelength detects the polyhapten reagent, and the third wavelength serves as a blank, and wherein the first wavelength is about 340 nm, and the second wavelength is about 293 nm, and the third wavelength is about 700 nm;

(D) measuring absorbance values at the first, second, and third wavelengths at at least two time points following a time delivery of the polyhapten reagent, wherein absorbance values at the first wavelength provide an indication of a concentration value for HbA1c, absorbance values at the second wavelength provide an indication of the polyhapten reagent, and wherein there is minimal to no protein/peptide detection at the third wavelength;

(E) extrapolating an absorbance value for the polyhapten reagent at the time of delivery thereof using a regression of absorbance values measured at the second and third wavelengths at two time points following the time of delivery of the polyhapten reagent; and (F) reporting to a user that a concentration value for HbA1c obtained by a separate algorithm has been flagged as unacceptable if the extrapolated absorbance value for the polyhapten reagent at the time of delivery thereof varies from a predicted value therefor by more than an established flag constant, the established flag constant set in order to flag results that are significantly impacted by incomplete delivery of the polyhapten reagent.

8. The method of claim 7, wherein in step (E), the first of the two time points following addition of the polyhapten reagent is about 7.2 seconds following addition of the polyhapten reagent, and wherein the second of the two points is about 7.2 seconds after the first time point.

9. The method of claim 7, wherein the biological sample is selected from the group consisting of urine, whole blood or any portion thereof, whole or lysed blood cells, saliva, sputum, cerebrospinal fluid, intestinal fluid, intraperitoneal fluid, cystic fluid, sweat, interstitial fluid, tears, mucus, bladder wash, semen, and combinations thereof.

10. A method of detecting aberrant results caused by incomplete delivery of a polyhapten reagent used in a glycated hemoglobin (HbA1c) inhibition immunoassay, the method comprising the steps of:

(A) inserting a reaction cuvette into a clinical chemistry analyzer system and reacting, within the reaction cuvette, a biological sample suspected of containing a target analyte comprising HbA1c with an anti-HbA1c antibody to the target analyte, thereby forming a soluble HbA1c-antibody complex;

(B) adding a polyhapten reagent to the reaction cuvette, wherein the polyhapten reagent comprises multiple copies of an epitope of HbA1c to which the anti-HbA1c antibody binds, and wherein the polyhapten reagent reacts with excess anti-HbA1c antibody to form an insoluble polyhapten/anti-HbA1c antibody complex;

(C) irradiating the reaction cuvette with light at at least three wavelengths, wherein a first wavelength turbidimetrically detects the insoluble polyhapten/anti-HbA1c complex, the second wavelength detects the polyhapten reagent, and the third wavelength serves as a blank;

(D) measuring absorbance values at multiple time points at at least three wavelengths following addition of the polyhapten reagent, wherein:

(i) a first wavelength is about 340 nm and turbidimetrically detects the insoluble polyhapten/anti-HbA1c antibody complex;

(ii) a second wavelength is about 293 nm and detects the polyhapten reagent; and (iii) a third wavelength serves as a blank whereby there is minimal to no protein/peptide detection at said wavelength, and wherein the third wavelength is about 700 nm;

(E) extrapolating an absorbance value for the polyhapten reagent at the time of delivery thereof using a regression of absorbance values measured at the second and third wavelengths at two time points following the time of delivery of the polyhapten reagent; and (F) reporting to a user that a concentration value for HbA1c obtained by a separate algorithm has been flagged as unacceptable if the extrapolated absorbance value for the polyhapten reagent at the time of delivery thereof varies from a predicted value therefor by more than an established flag constant, the established flag constant set in order to flag results that are significantly impacted by incomplete delivery of the polyhapten reagent.

11. The method of claim 10, wherein in step (E), the first of the two time points following addition of the polyhapten reagent is about 7.2 seconds following addition of the polyhapten reagent, and wherein the second of the two points is about 7.2 seconds after the first time point.

12. The method of claim 10, wherein the biological sample is selected from the group consisting of urine, whole blood or any portion thereof, whole or lysed blood cells, saliva, sputum, cerebrospinal fluid, intestinal fluid, intraperitoneal fluid, cystic fluid, sweat, interstitial fluid, tears, mucus, bladder wash, semen, and combinations thereof.

13. The method of claim 1, further comprising the step of instructing the user to repeat steps (A)-(F) if step (F) reports to the user that a concentration value for the target analyte obtained by a separate algorithm has been flagged.

14. The method of claim 7, further comprising the step of instructing the user to repeat steps (A)-(F) if step (F) reports to the user that a concentration value for HbA1c obtained by a separate algorithm has been flagged.

15. The method of claim 10, further comprising the step of instructing the user to repeat steps (A)-(F) if step (F) reports to the user that a concentration value for HbA1c obtained by a separate algorithm has been flagged.

* * * * *